(12) United States Patent
Rangarajan et al.

(10) Patent No.: US 6,795,201 B2
(45) Date of Patent: Sep. 21, 2004

(54) METHOD OF OBJECTIVELY EVALUATING A SURFACE MARK

(75) Inventors: Pratima Rangarajan, Clifton Park, NY (US); Vicki Herzl Watkins, Alplaus, NY (US); Kevin George Harding, Niskayuna, NY (US); John William Devitt, Mainville, OH (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/394,673

(22) Filed: Mar. 21, 2003

(65) Prior Publication Data

US 2003/0179371 A1 Sep. 25, 2003

Related U.S. Application Data

(63) Continuation-in-part of application No. 09/617,972, filed on Oct. 18, 2000, now abandoned.
(60) Provisional application No. 60/163,357, filed on Nov. 3, 1999.

(51) Int. Cl.$^7$ .............................................. G01B 11/22
(52) U.S. Cl. ........................................... 356/626; 73/82
(58) Field of Search .............................. 356/626, 237.1, 356/237.2–237.5; 33/18.1, 32.1, 124; 73/78–85; 136/124

(56) References Cited

U.S. PATENT DOCUMENTS

| | | | |
|---|---|---|---|
| 4,502,225 A | | 3/1985 | Lin |
| 4,627,096 A | * | 12/1986 | Grattoni et al. ............. 382/141 |
| 4,641,017 A | | 2/1987 | Lopata |
| 4,991,967 A | * | 2/1991 | Creighton ................... 356/606 |
| 5,185,638 A | * | 2/1993 | Conzola et al. .......... 356/237.2 |
| 5,355,721 A | * | 10/1994 | Las Navas Garcia .......... 73/82 |
| 5,386,481 A | | 1/1995 | Hine et al. |
| 5,774,212 A | | 6/1998 | Corby, Jr. |
| 6,247,355 B1 | * | 6/2001 | Suresh et al. ................... 73/82 |

FOREIGN PATENT DOCUMENTS

| | | |
|---|---|---|
| JP | 06 066528 | 3/1994 |
| JP | 08 037168 | 2/1996 |
| JP | 09 061365 | 3/1997 |
| WO | WO 95 10097 | 4/1995 |
| WO | WO 95 35506 | 12/1995 |

OTHER PUBLICATIONS

Watanabe, et al., Telecentric Optics for Computational Vision, Proceedings of Image Understanding Workshop, Palm Springs (Feb. 1996).*

P. Rangarajan et al, "Scratch visibility of Polymers Measured Using Optical Imaging", Polymer Engineering and Science, vol. 43, No. 3, Mar. 2003.

Gordon Research Conference on "Coatings & Films", Colby Sawyer College, New London, New Hampshire presented on Jul. 19, 2001.

SAE 2001 World Congress, Mar. 2001, Detroit, MI USA presented on Mar. 5, 2001.

American Physical Society Meeting, Indianapolis, Indiana presented on Mar. 20, 2002.

* cited by examiner

Primary Examiner—Richard A. Rosenberger
Assistant Examiner—Vincent P. Barth
(74) Attorney, Agent, or Firm—Kimberly H. Parker; Patrick K. Patnode

(57) ABSTRACT

A method of objectively evaluating a surface mark provides an objective test methodology for the optical quantification of surface marks. The method may include the steps of reproducibly producing a surface mark on an object and optically evaluating the surface mark. The surface mark may be reproducibly produced by loading a stylus, contacting a surface on the object with the loaded stylus and moving the object and the surface thereon relative to the loaded stylus so as to thereby produce a mark on the surface. Any surface mark is optically evaluated by optically producing images of the surface mark, electronically capturing the optically produced images and measuring selected parameters of the captured optically produced images.

23 Claims, 5 Drawing Sheets

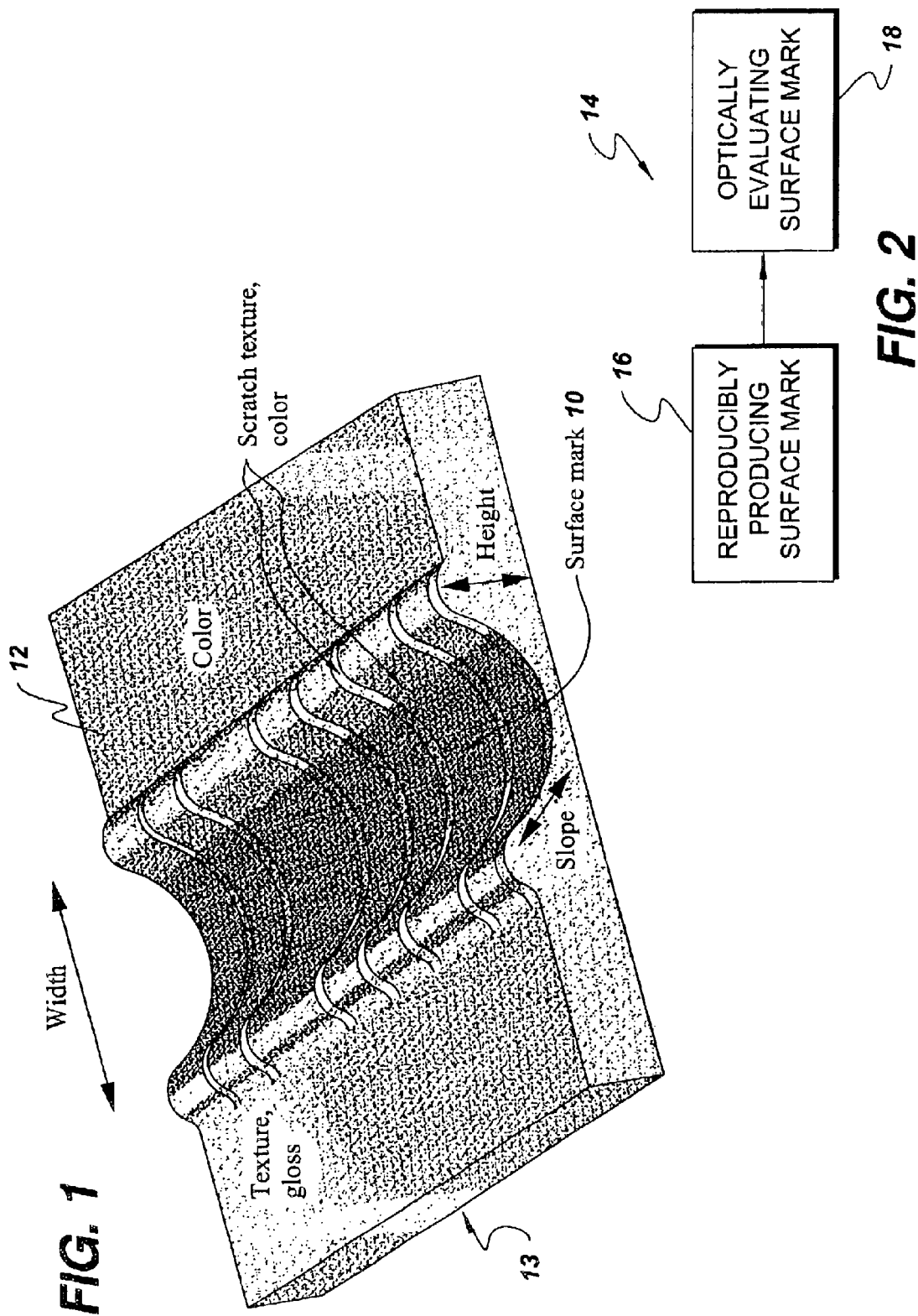

METHOD OF OBJECTIVELY EVALUATING A SURFACE MARK

This application is a continuation-in-part of U.S. application Ser. No. 09/617,972, filed Oct. 18, 2000 now abandoned, which claims the benefit of U.S. Provisional Application Serial No. 60/163,357 filed Nov. 3, 1999.

BACKGROUND OF THE INVENTION

The present invention generally relates to surface marks on objects and, more particularly, is concerned with a method of objectively evaluating a surface mark. The term "mark" as used hereinafter means any visible trace or impression on a surface, such as a line, dot, spot, stain, scratch, mar, blemish, dent, bruise, etc., on the surface.

A human observer perceives a mark on a surface of an object, such as an automotive body panel, as a point of contrast from the rest of the surface. The contrast seen by the human observer is affected by the size, color and gloss of the mark as well as of the surface that is marked. However, any attempt at visual quantification of the contrast by the human observer will necessarily be subjective and vary from one human observer to the next.

A review of the prior literature and patent art reveals the absence of an objective approach to optical quantification of surface marks. Thus, heretofore the evaluation of surface marks has been mainly dependent upon the subjective perception of the human observer making the evaluation.

Consequently, a need exists for an innovation which will provide an objective approach to quantification of surface marks.

BRIEF SUMMARY OF THE INVENTION

In one embodiment the present invention provides a method of objectively evaluating a surface mark which is designed to satisfy the aforementioned need. Thereto, the method of the present invention provides a reliable objective test methodology for optical quantification of surface marks which avoids the subjectivity of human visual perceptions of surface marks.

In one embodiment the present invention is a method of objectively evaluating a surface mark, comprising the steps of:
reproducibly producing a surface mark on an object; and
optically evaluating the surface mark by optically producing images of the surface mark by (i) illuminating the surface mark at a first angle relative to a reference plane extending substantially perpendicular to the surface mark; and (ii) capturing an image of the illuminated surface mark at a second angle relative to the reference plane, wherein the orientation of the surface mark in the plane of the sample surface is horizontal to image detector means.

BRIEF DESCRIPTION OF THE DRAWINGS

FIG. 1 is an enlarged perspective view of a mark on a surface which can be evaluated by the method of the present invention.

FIG. 2 is a general block diagram of steps of the method in one embodiment of the present invention.

DETAILED DESCRIPTION OF THE INVENTION

Figure 3:
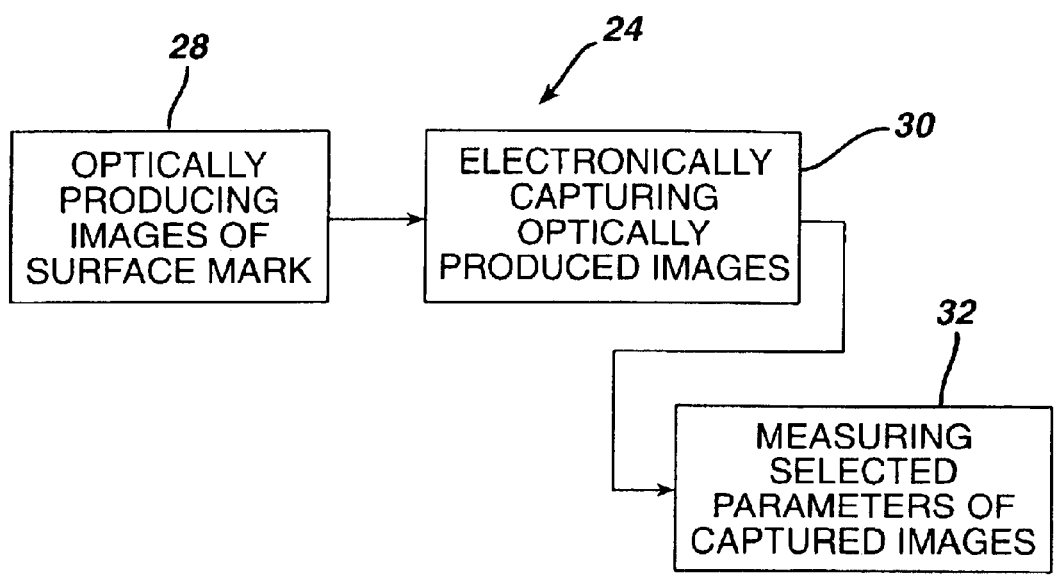
FIG. 3 is a more detailed block diagram representing further steps of the method of the present invention.

Referring now to the drawings, there is illustrated in FIG. 1 an example of a mark 10, such as a scratch, on a surface 12 of a sample object 13 (that is termed "evenly illuminated sample" in FIGS. 5 and 6) which can be evaluated by the method of the present invention, being set forth in one embodiment by block diagram 14 of FIG. 2. As shown in block diagram 14, steps of the surface mark objective evaluation method in one embodiment of the present invention include, first, reproducibly producing the surface mark 10 as per block 16 and, second, optically evaluating the surface mark 10 as per block 18. The surface mark 10 can be reproducibly produced by using a first equipment setup, such as diagrammatically represented in FIG. 4 and generally designated 20.

Figure 5:
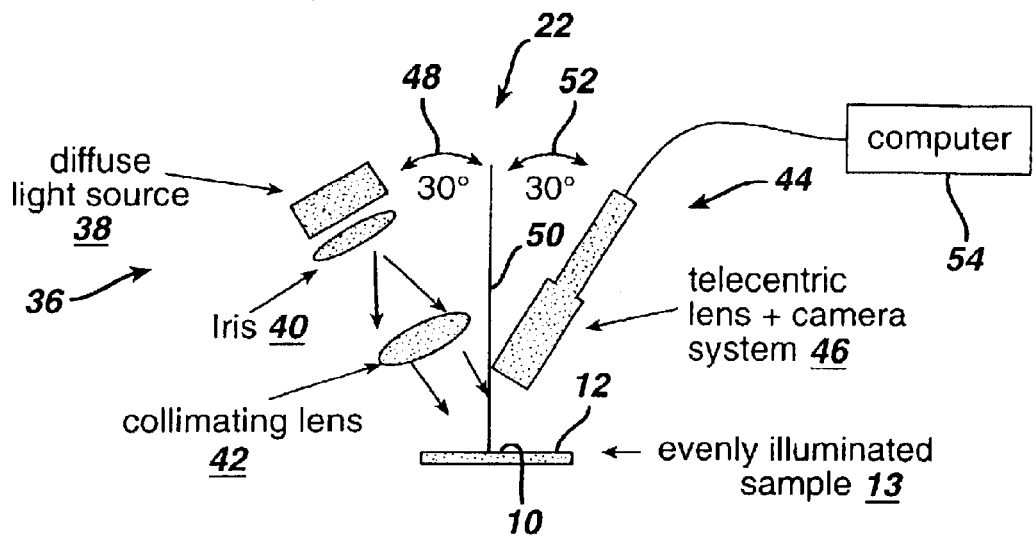
FIG. 5 is a diagrammatic representation of an equipment setup for measuring the optical quality of a surface mark relative to the surrounding surface.
Figure 6:
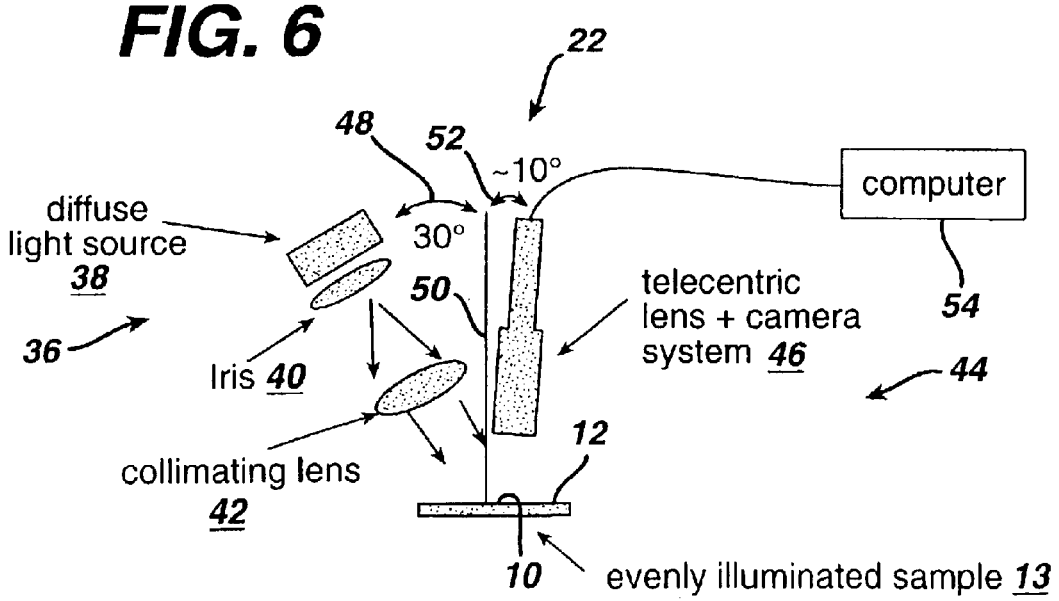
FIG. 6 is a diagrammatic representation of an equipment setup for measuring the optical quality of a surface mark relative to the surrounding surface.

Any surface mark 10, either reproducibly produced by using the apparatus in one embodiment of the present invention, or preexisting, or having been produced by any means, can be optically evaluated by using a second equipment setup, such as diagrammatically represented in FIGS. 5 and 6 and generally designated 22. The method of the present invention in one embodiment is set forth in more detail by the block diagram 24 shown in FIG. 3. As shown in block diagram 24, the surface mark objective evaluation method in one embodiment of the present invention comprises optically evaluating a surface mark which includes steps of, first, optically producing images of the surface mark 10 as per block 28 that simulate human visual perceptions of the surface mark, second, electronically capturing the optically produced images of the surface mark 10 as per block 30 and, third, measuring selected parameters of the captured optically produced images of the surface mark 10 as per block 32.

Figure 4:
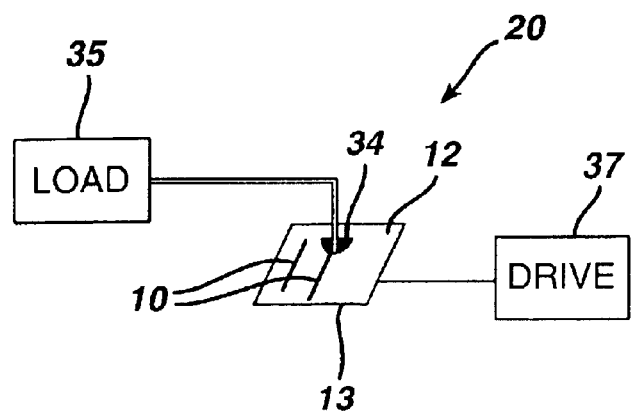
FIG. 4 is a diagrammatic representation of an equipment setup for producing reproducible marks on surfaces.

Referring to FIGS. 4–6, as mentioned above there is illustrated the first and second equipment setups 20, 22 for carrying out the steps of the method of the present invention in one embodiment. FIG. 4 diagrammatically depicts the surface mark 10 being reproducibly produced by using a suitable device such as a stylus 34 of the first equipment setup 20. A desired load 35 is applied to the stylus 34 such as by use of a transducer with a voltage feedback loop or with a dead weight. The loaded stylus 34 is brought into contact with the surface 12 on the object 13, and the object 13 and surface 12 thereon are moved, such as reciprocally, by a suitable drive device 37 relative to the loaded stylus 34 so as to produce the mark 10 on the surface 12. The geometry and size of the stylus 34 can be varied. Conical and spherical stylii with varied tip sizes and tip angles can be used. The material of the stylus 34 may vary. Stainless steel and diamond are commonly used. The rate at which the surface mark 10 is applied or produced may be varied by the speed of translation of the body. The equipment setup 20 facilitates the reproducible production of surface marks 10 of uniform size (depth, width, ridge heights) on any type surface, even in parts that are curved, warped or have any type of unevenness in surface height because the loaded stylus is floating and follows the contour of the surface of the sample.

FIGS. 5 and 6 diagrammatically depict the surface mark 10 being optically evaluated by the second equipment setup 22 which includes illumination means 36 in the form of a light source 38 (either white light or laser light) and optical components such as an iris 40 (variable aperture) and a lens 42 which provide either collimated or diffuse light to provide even illumination of the surface mark 10 and at least one image detector means 44 in the form of at least one telecentric lens and camera system 46 which optically captures and produces images of the surface mark 10. The iris 40 may be positioned at the focal length of the lens 42. The lens 42 serves to collimate the light from the location of the aperture of the iris 40, with a spread of collimated light beams being determined by the size of the aperture. That is, the light everywhere after the collimating lens 42 will contain a range of angles of light paths which will be the same range of angles and the same intensity of light at every position within the light field. This condition causes the lighting to be so called telecentric, one focal length beyond the collimating lens 42. This light is aimed at the surface mark 10 at a range of angles. The optical image that is produced may be correlated to human visual perception of the surface mark 10. The camera viewing system 46 incorporates a telecentric viewing lens, with a variable aperture at the focal length of the collimating lens 42 and positioned to collect an equal amount and equal range of viewing angles of light from every point on the mark 10 and surface 12. The illumination and detection system is suitable for opaque, translucent, and transparent samples. The video camera system 46 is a detector that measures the light reflected or transmitted (for transparent bodies) and is positioned at the focus of the telecentric viewing lens so as to detect the image formed from the scattering/reflectance from the mark 10 on the surface 12. Intensity values may also be measured by the detector. The system 46 may be positioned at various angles ranging from the specular position relative to the illumination means 36, to just off specular, to other angles up to normal to the surface 12. More than one image detector means 44, for example in the form of more than one telecentric lens and camera system 46, may be present The surface mark 10, either reproducibly produced by using the apparatus in one embodiment of the present invention, or preexisting, or having been produced by any means, is illuminated at a first angle 48 relative to a reference plane 50 extending substantially perpendicular or normal to the surface mark 10. The image of the illuminated surface mark is detected or captured at a second angle 52 relative to the reference plane 50. In the arrangement of the second equipment setup 22 shown in FIG. 5, the first and second angles 48, 52 are substantially the same for optically evaluating the dimensions of the surface mark 10. The first and second angles 48, 52 could be varied in order to capture all points of contrast. This equipment setup 22 of FIG. 5 will capture the effects of the size, sharpness, and contrast of the surface mark 10 as well as the average intensity of the mark 10 and the average intensity of surface 12 surrounding the mark. In the modified arrangement of the second equipment setup 22 shown in FIG. 6, the first and second angles 48, 52 are different for optically evaluating the image quality of the surface mark 10. The first angle 48 remains the same as before relative to the normal reference plane 50. The second angle 52 selected is less than the first angle 48 relative to the normal reference plane 50. However, the second angle 52 could be varied to achieve maximum contrast between the surface mark 10 and its surroundings. This equipment setup 22 of FIG. 6 will capture the size, sharpness and average intensity of the surface mark 10 and the average intensity of the surroundings. The image quality is optimized by adjusting the aperture in the lens 42 of the illumination means 36 so as to provide even illumination on the mark 10 and surface 12 and minimize the variations due to ripples or warpage of the surface 12. The viewing aperture is then adjusted to maximize the clarity of the mark 10 as seen in the image. The mark images are analyzed for size, sharpness, and contrast of the mark as well as the average intensity of the mark 10 and surface 12 surrounding the mark. In the context of the invention "surroundings" or "surface surrounding the mark" are defined as any or all area outside of the mark which is not part of the mark in question.

Also seen in FIGS. 5 and 6, a computer 54 is connected to the one or more telecentric lens and camera systems 46 for electronically capturing the optically produced images of the surface mark 10. The computer 54, which can be a conventional personal computer with sufficient memory, stores and operates commercially-available conventional image capture software so as to measure parameters of the images of the surface mark 10. Examples of suitable image capture software are Matrox Inspector Mateor 2 and Image Pro or Sherlock. The parameters of the captured optically produced images of the surface mark 10 include the size, sharpness, and contrast of the surface mark 10 relative to the surrounding surface 12, as well as the average intensity of the mark 10 and surface 12 surrounding the mark 10 in both variations of the second equipment setup. The pictures from the camera system 46 are acquired using the software of the computer 54 and data is extracted from it in a known manner. The data from the images are processed by the computer 54 to provide values that can be related to gloss, color, surface mark texture and size or dimensions, as well as visual quality of the mark. The selection of at least one set, preferably two sets, of first and second angles 48, 52 to produce optical images is typically sufficient to generate parameters for adequate characterization of a surface mark. For example, illustrative sets of first and second angles may include a first set of first and second angles such as each thirty or sixty degrees off the normal reference plane 50 (which is the position to collect the specularly reflected light from the mark 10 and surface 12), and a second set of first and second angles such as thirty and ten degrees, respectively, off the normal reference plane 50. Data generated at different angles of illumination may be collected using more than one image detector means 44, for example in the form of more than one telecentric lens and camera systems 46, and then processed using computer 54.

Figure 7A:
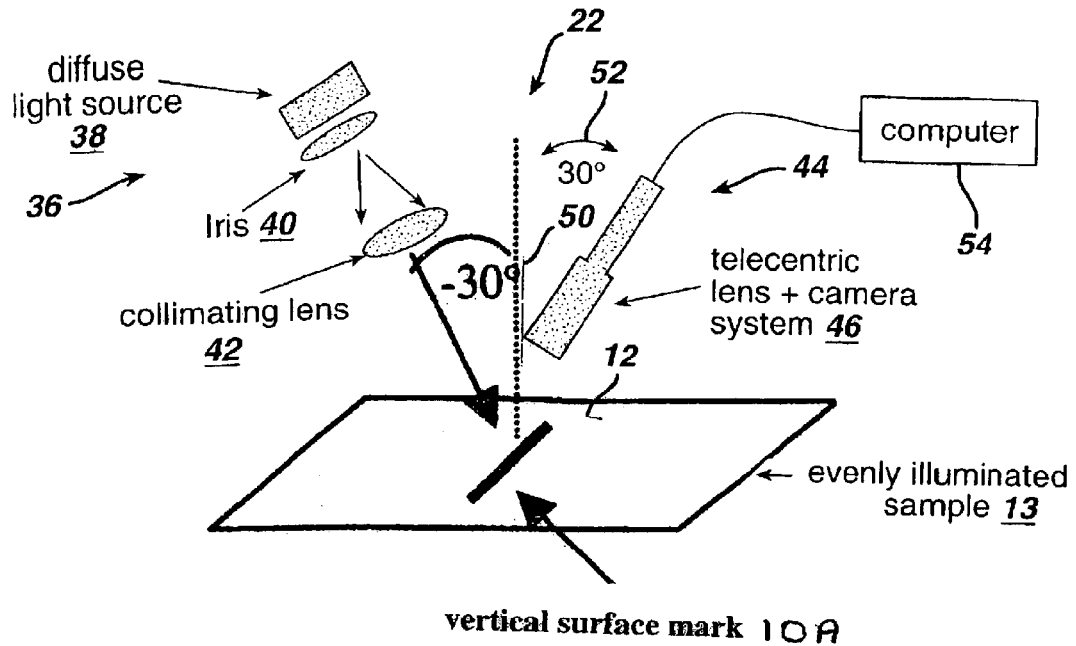
FIG. 7 is a diagrammatic representation of possible surface mark orientations relative to an orientation of incident beam and detector systems.
Figure 7B:
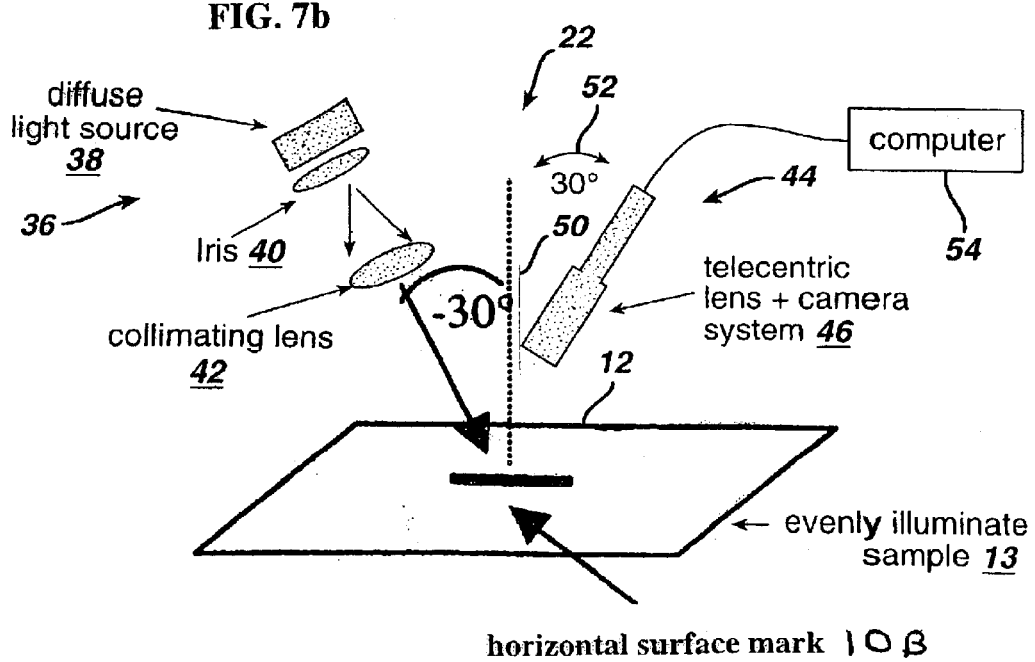

The light reflected from an optically smooth surface will be primarily concentrated along the specular angle, wherein angle of incidence equals angle of reflection. In one particular embodiment of the invention an angle of incidence of minus 30 degrees is chosen as a compromise between loss of contrast (at lower angles of incidence) and loss of light from the bottom of the surface mark 10 (at high angles of incidence). The fraction of light collected at the specular angle may be used to calculate specular gloss. As seen in FIGS. 7a and 7b, the orientation of surface mark 10 to the image detector means 44, for example in the form of telecentric lens and camera system 46, may be vertical (10a) or horizontal (10b). In a particular embodiment the surface mark 10 is oriented horizontally (as in surface mark 10b) to the image detector means 44 as in FIG. 7b. In the present context the term "vertical orientation" means that the length of the surface mark is oriented at an angle of 90 degrees to the image detector means, and the term "horizontal orientation" means that the length of the surface mark is oriented at an angle of 0 degrees to the image detector means. Although only one set of first and second angles is shown in FIGS. 7a and 7b, it should be understood that other values for first and second angles are also operative. In order to collect optical information from multiple (i.e. more than one) surface marks 10 oriented at various angles to each other and, hence, at various angles to the image detector means 44, for example in the form of telecentric lens and camera system 46, the sample surface 12 may be incrementally rotated in a plane to present various surface marks 10 oriented horizontally (as in surface mark 10b) to the image detector means 44. The resultant data from individual surface marks 10 may be analyzed separately. Related information is contained in "Scratch Visibility of Polymers Measured Using Optical Imaging" by P. Rangarajan, M. Sinha, V. Watkins and K. Harding, "Polymer Engineering and Science", vol. 43, No. 3, March 2003, which is incorporated herein in its entirety.

Figure 8:
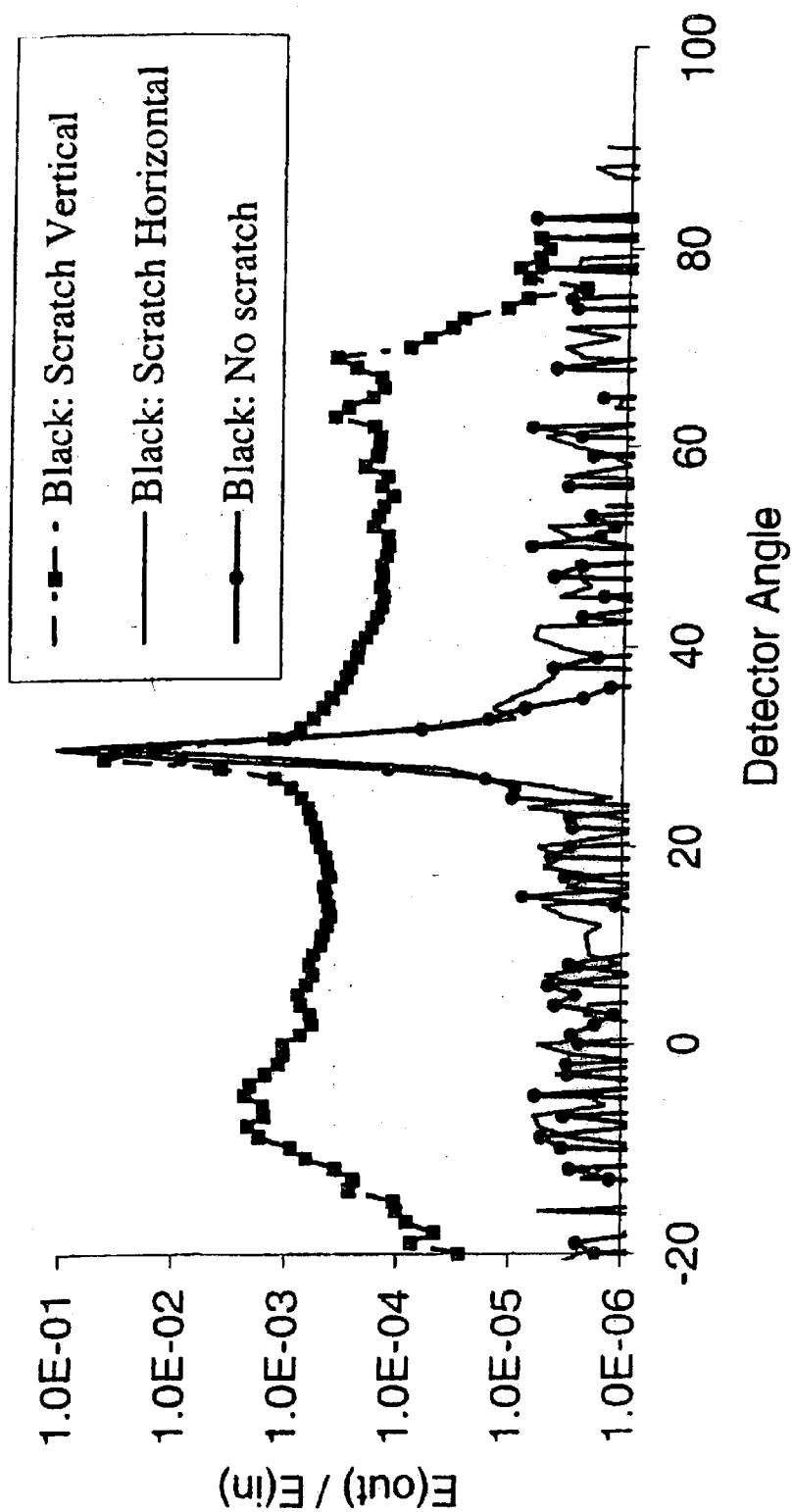
FIG. 8 shows scattering intensity from a surface mark oriented vertically versus scattering intensity from a surface mark oriented horizontally relative to incident light from a laser illumination means.

Independent measurement of off-specular scattering typically requires exclusion of all specular reflections from the chosen off-specular angle. The presence of a surface mark 10 on surface 12 results in some loss in specular intensity, which may result in a concomitant increase in intensity at off-specular angles. FIG. 8 shows scattering intensity from a surface mark oriented vertically versus scattering intensity from a surface mark oriented horizontally relative to incident light from an illumination means. The data for FIG. 8 were generated using a laser illumination means in a bidirectional reflectance distribution function (BRDF) experiment. When surface mark 10 is oriented horizontally (as in surface mark 10b), the reflections off the contours of the mark are rotated off the plane of incidence and are absent in the measurement at all angles. The scattering profile from the vertically oriented surface mark 10a shows a decrease in specular intensity accompanied by broad low-intensity shoulders between about minus 5 degrees and about 25 degrees and between about 35 degrees and about 70 degrees. These shoulders are the reflections from the surface mark contours that are rotated in the plane of incidence with respect to the reflections from the sample surface at 30 degrees. In the vertical alignment therefore, the reflections due to the surface mark contours will result in a loss of intensity at the specular angle with a concomitant increase in intensity at a range of off-specular angles. Thus, the independent measurement of off-specular scattering will be compromised by the presence of the specular reflections from the surface mark contours as shown in FIG. 8. For independent measurement of diffuse scattering at off-specular angles it is therefore preferred that the orientation of surface mark 10 be horizontal in the plane of sample surface 12.

The relationship between the type of mark 10, its dimensions and its optical qualities are used to understand and design materials. The method can also be used to study multiple marks applied with or without order. The combination of mark dimension and optical quality measurement can also be applied to parts that have been scratched or marked by other methods. The parts tested can be monolithic or coatings or cap layers. Any type of material which is capable of being marked, scratched or marred, can be employed as the substrate or body in the method of the present invention. Illustrative materials include thermoplastics and blends of thermoplastics, thermosets and blends of thermosets, blends of thermosets and thermoplastics, composites, glazing material, glass, stone, ceramic, leather, metal and cellulosic materials such as wood. In another embodiment the method of the invention also provides a method for objectively evaluating the susceptibility of a surface for receiving a mark.

The optical evaluation system shown in FIGS. 5 and 6 identifies pixels meeting certain criteria and characterizes the optical quality of a mark on a sample using at least one of five criteria; namely, (1) contrast (average deviation of a pixel from background), (2) size (number of pixels within the mark which meet criteria), (3) sharpness (first derivative of contrast, i.e., change in slope of contrast), (4) average pixel intensity of surrounding surface, and (5) average pixel intensity of mark. In preferred embodiments a combination of all five criteria is used to characterize the optical quality of a mark. Therefore, the method of characterizing a mark is not material dependent but can be used for any material with a surface mark.

The computer-generated data may be used to predict human perception of a surface mark characterized by the optical evaluation system. The data may also be used to predict the outcome or evaluate any repair process on a mark. Also, the method of the present invention may be used to evaluate an existing surface mark.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

What is claimed is:

1. A method of objectively evaluating a surface mark, comprising the steps of:
   reproducibly producing a surface mark on an object; and
   optically evaluating the surface mark by optically producing images of the surface mark by (i) illuminating the surface mark at a first angle relative to a reference plane extending substantially perpendicular to the surface mark; and (ii) capturing an image of the illuminated surface mark at a second angle relative to the reference plane by use of a telecentric lens and camera system, wherein the orientation of the surface mark in the plane of the sample surface is horizontal to image detector means.

2. The method of claim 1 in which the step of reproducibly producing a surface mark includes the further steps of:
   contacting a surface on the object with a stylus; and
   moving the object and thereby the surface thereon relative to the stylus so as to produce a mark on the surface.

3. The method of claim 2 in which the step of reproducibly producing a surface mark includes the further step of applying a load to the stylus such that the object and surface thereon are moved relative to the loaded stylus.

4. The method of claim 1 in which the first and second angles are substantially the same for optically producing images of a surface mark.

5. The method of claim 1 in which the first and second angles are substantially different for optically producing images of a surface mark.

6. The method of claim 1 in which at least two sets of images of the surface mark are produced, including one set in which the first and second angles are substantially the same, and one set in which the first and second angles are substantially different.

7. The method of claim 1 in which the surface mark is illuminated by use of a diffuse light source.

8. The method of claim 1 in which the surface mark is illuminated by use of a collimated light source.

9. The method of claim 1 in which the step of optically evaluating the surface mark includes the step of electronically capturing the optically produced images of the surface mark.

10. The method of claim 9 in which the step of electronically capturing the optically produced images of the surface mark includes the use of a computer connected to the telecentric lens and camera system.

11. The method of claim 10 in which the step of optically evaluating the surface mark includes the step of measuring parameters of the captured optically produced images of the surface mark by the use of image capture software stored and operated by the computer.

12. The method of claim 11 in which the parameter of the captured optically produced images of the surface mark include size, sharpness, and contrast of the surface mark relative to the surrounding surface, and the average intensity of the mark and surface surrounding the mark.

13. A method of objectively evaluating a surface mark, comprising the steps of:

reproducibly producing a surface mark on an object;

optically evaluating the surface mark by optically producing images of the surface mark by (i) illuminating the surface mark at a first angle relative to a reference plane extending substantially perpendicular to the surface mark; and (ii) capturing an image of the illuminated surface mark at a second angle relative to the reference plane by use of a telecentric lens and camera system, wherein the orientation of the surface mark in the plane of the sample surface is horizontal to image detector means; and measuring selected parameters of the captured optically produced images of the surface mark.

14. The method of claim 13 in which the step of reproducibly producing a surface mark includes the further steps of:

applying a load to a stylus;

contacting a surface on the object with the loaded stylus; and moving the object and thereby the surface thereon relative to the loaded stylus so as to produce a mark on the surface.

15. The method of claim 13 in which at least two sets of images of the surface mark are produced, including one set in which the first and second angles are substantially the same and one set in which the first and second angles are substantially different.

16. The method of claim 13 in which the step of optically evaluating the surface mark includes the step of electronically capturing the optically produced images of the surface mark, said step of electronically capturing the optically produced Images of the surface mark includes the use of a computer connected to the telecentric lens and camera system.

17. The method of claim 16 in which the step of measuring selected parameters of the captured optically produced images of the surface mark is performed by the use of image capture software stored and operated by the computer.

18. The method of claim 17 in which the parameters of the captured optically produced images of the surface mark include size, sharpness, and contrast of the surface mark relative so the surrounding surface, and the average intensity of the mark and surface surrounding the mark.

19. A method of objectively evaluating a surface mark, comprising the steps of:

optically evaluating the surface mark by optically producing images of the surface mark by (i) illuminating the surface mark at a first angle relative to a reference plane extending substantially perpendicular to the surface mark; and (ii) capturing an image of the illuminating surface mark at a second angle relative to the reference plane by use of a telecentric lens and camera system, wherein the orientation of the surface mark in the plane of the sample surface is horizontal to image detector means; and measuring selected parameters of the captured optically produced images of the surface mark.

20. The method of claim 19 in which at least two sets of images of the surface mark are produced, including one set in which the first and second angles are substantially the same, and one set in which the first and second angles are substantially different.

21. The method of claim 19 in which the step of optically evaluating the surface mark includes the step of electronically capturing the optically produced images of the surface mark, said step of electronically capturing the optically produced images of the surface mark includes the use of a computer connected to the telecentric lens and camera system.

22. The method of claim 21 in which the step of measuring selected parameters of the captured optically produced images of the surface mark is performed by the use of image capture software stored and operated by the computer.

23. The method of claim 22 in which the parameters of the captured optically produced images of the surface mark include size, sharpness, and contrast of the surface mark relative to the surrounding surface, and the average intensity of the mark and surface surrounding the mark.

* * * * *